United States Patent
Raz et al.

(10) Patent No.: US 6,230,154 B1
(45) Date of Patent: May 8, 2001

(54) DATABASE ELEMENT RETRIEVAL BY EXAMPLE

(75) Inventors: Ryan S. Raz, Toronto; Iouri Lappa, North York, both of (CA)

(73) Assignee: Morphometrix Technologies Inc., Toronto (CA)

( * ) Notice: Subject to any disclaimer, the term of this patent is extended or adjusted under 35 U.S.C. 154(b) by 0 days.

(21) Appl. No.: 09/115,608

(22) Filed: Jul. 15, 1998

Related U.S. Application Data

(60) Provisional application No. 60/052,618, filed on Jul. 15, 1997.

(51) Int. Cl.[7] .................................................. G06F 17/30
(52) U.S. Cl. ................... 707/3; 707/2; 707/104; 707/4; 707/5
(58) Field of Search .................... 707/1, 3, 4, 5, 707/7, 100; 395/605, 602, 600, 414; 364/419

(56) References Cited

U.S. PATENT DOCUMENTS

| | | | |
|---|---|---|---|
| 5,197,005 | * 3/1993 | Shwrtz et al. ...................... | 364/419 |
| 5,442,780 | * 8/1995 | Takanashi et al. ................... | 395/600 |
| 5,577,241 | * 11/1996 | Spencer ................................ | 395/605 |
| 5,600,831 | * 2/1997 | Levy et al. .......................... | 395/602 |
| 5,742,815 | * 4/1998 | Stern .................................... | 395/414 |
| 5,826,261 | * 10/1998 | Spencer ................................ | 705/5 |

* cited by examiner

Primary Examiner—Thomas Black
Assistant Examiner—Thuy Do
(74) Attorney, Agent, or Firm—Ridout & Maybee

(57) ABSTRACT

A system and method for database element retrieval. A query comprises identifying which elements in the database are close or similar to an example which is specified in the query. The query is performed by defining a hyper-box that surrounds the example in the database space. Once the hyper-box is defined, the elements contained within the hyper-box will be close or similar to the example in the query. The elements contained in the hyper-box may be subsequently ranked in the database space using a Euclidean concept of distance.

6 Claims, 4 Drawing Sheets

DATABASE ELEMENT RETRIEVAL BY EXAMPLE

This application claims the benefit of Provisional application 60/052,618 filed Jul. 15, 1997.

FIELD OF THE INVENTION

This invention relates to a system for storing and retrieving database elements, and more particularly to a method for retrieving elements residing in a collection of elements based on the similarity to an external or query example.

BACKGROUND OF THE INVENTION

Large quantities of data are typically collected and stored in some sort of organized format, such as a database. It is often desirable to locate a number of elements within the collection that are similar to a specific query example. The problem of performing a search for such similar elements comes down to the definition of "similar".

The present invention provides a database element retrieval system and method in which elements are retrieved from the database on the basis of their similarity to an external example or query.

SUMMARY OF THE INVENTION

The present invention comprises a database element retrieval system. According to the invention, database elements are retrieved on the basis of their "similarity" to an external example or query example.

In a first aspect, the present invention provides a database element retrieval system comprising: (a) means for storing a plurality of elements, (b) means for processing an external query, said means for processing including, (i) means for generating search parameters associated with said query, (ii) means for determining a classification for said query, (iii) means for setting a search range in the database for said query, (iv) means for establishing a search space in the database, said search space being based on said search range and said classification, (v) means for retrieving a plurality of elements from said search space in response to said query.

In another aspect, the present invention provides a method for retrieving one or more elements from a database in response to a query, said method comprising the steps of: (a) generating search parameters associated with said query, (b) determining a classification for said query, (c) setting a search range in the database for said query, (d) establishing a search space in the database, said search space being based on said search range and said classification, (e) retrieving a plurality of elements from said search space in response to said query.

BRIEF DESCRIPTION OF THE DRAWINGS

Reference will now be made to the accompanying drawings, which show by way of example, a preferred embodiment of the present invention, and in which.

DETAILED DESCRIPTION OF THE PREFERRED EMBODIMENT

The present invention comprises a database element retrieval system and method. As will be described, it is a feature of the invention that a database element is retrieved on the basis of its "similarity" to an external example or query. Although the database element retrieval system is described in the context of an automated system for cytological specimens, it will be appreciated that the database element retrieval system has wider applicability.

Figure 1:
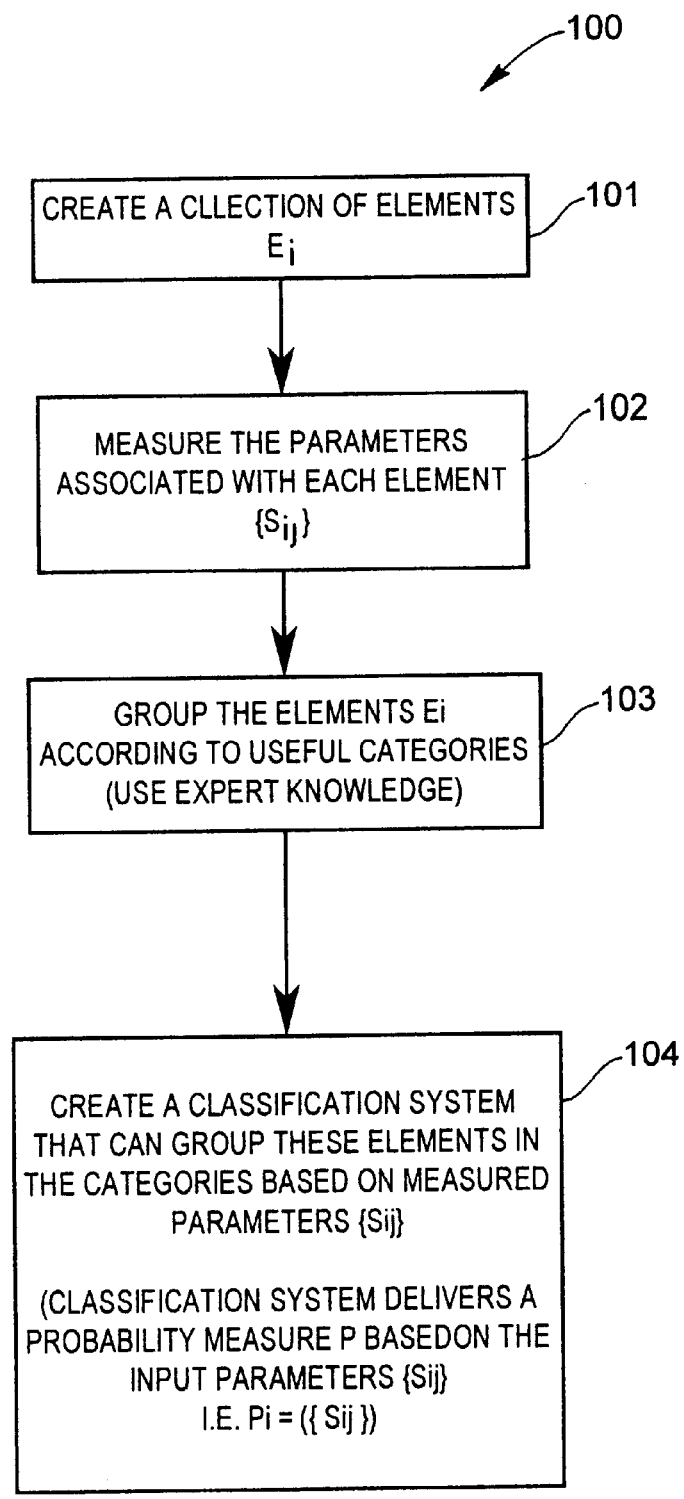
FIG. 1 shows in flow chart form the method steps for creating a database retrieval system according to the invention.

Reference is first made to FIG. 1 which shows in flowchart form a method 100 for creating a database for storing a collection of elements $E_i$ for later retrieval. (A method 200 for retrieving similar elements $E_i$ from the collection is described below with reference to FIG. 2.)

As shown in FIG. 1, the first step (block 101) in creating the database involves creating a collection of elements $E_i$, where $E_i$ is the $i^{th}$ element in the collection. If each element $E_i$ in the collection can be described by a set of numerical parameters then these may be used to define similarity. For example, if the elements in the collection are images of cytological specimens, then the numerical parameters may relate to the size, colour, texture, and shape of the imaged objects.

The next step (block 102) comprises measuring the parameters associated with each element $E_i$. For each element $E_i$ in the collection, there is a set of numerical parameters denoted by $\{S_{ij}\}$, where $S_{ij}$ is the $j^{th}$ parameter of the element $E_i$. Accordingly, the definition of similarity is expressed as all of those elements in the collection whose numerical parameters are, to some degree, close to the query example. All of this information is then stored in a database of suitable design as will be within the understanding of one skilled in the art. Thus, given a complete set of numerical parameters, $\{S_{ij}\}$, the element $E_i$ can be recovered from the database.

The following step (block 103) comprises grouping the elements $E_i$ according to categories of expert knowledge based on the application. The form of the expert knowledge will depend on the particular application. For example, in the context of cytological specimen testing the range of cell types may be very large so expert knowledge derived from experts, such as cytotechnologists and pathologists, is utilized to provide groupings according to expected cell types. In the alternative, the groupings may simply comprise Normal or Abnormal cell types.

With the definition of similarity described above, a search of the collection of elements may be performed once a level of closeness or similarity is ascertained for the query example. One way to do this is to specify each of the acceptable ranges of the numerical parameters $\{\Delta S_{ij}\}$ on an ad hoc basis. There are two drawbacks to this approach. First, it is difficult for a human observer to suggest each of the appropriate ranges, $\Delta S_{ij}$, because there is often no intuitive grasp of the meaning of each of these parameters. Second, there is no way for the human observer to determine the inter-relationships between these parameters and their relative importance in determining similarity. Indeed, there is no way for this person to discover the local variations in the relative importance.

In another aspect, rather than establishing the acceptable ranges of the numerical parameters, $\{\Delta S_{ij}\}$, the human observer establishes the number of elements $E_i$ that must be found in the search of the collection. It will be appreciated that the acceptable ranges of the numerical parameters $\{\Delta S_{ij}\}$ must be defined dynamically so that the search region can be adjusted to meet this criterion.

Accordingly, in the preferred embodiment, the method includes a classification step (block 104). The classification step 104 comprises creating a classification system which groups the elements $E_i$ in categories based on the measured parameters $\{S_{ij}\}$. The classification system introduced to the collection of elements $E_i$ may be analytically-based or may be a numerical system. The principal requirement is that the classification function relate a set of numerical parameters $\{\Delta S_{ij}\}$ to a unique value $P_i$, where $P_i$ is the output value of the classifier and can be used to place the element, $E_i$ into one of two categories. The classification system comprises a probability function where P is a probability measure based on the input parameters $\{S_{ij}\}$, i.e. for the element $E_i$, $P_i = P[\{S_{ij}\}]$, where j refers to the range of the numerical parameters. It will be appreciated that the probability function, $P[\{S_{ij}\}]$ should be continuous over the numerical parameter space of interest. The classification system may comprise any one of a number of models, including for example, statistical pattern recognition, discriminant analysis or fuzzy logic, and the utilization of a particular model will depend on the application as will be within the understanding of one skilled in the art.

The classification system derived in step 104 of the method 100 provides a compact representation of the organization of the elements $E_i$ in the collection according to the human experts that assembled the collection. By using expert knowledge to define the classification categories, the classification system (i.e. classifier) provides a measure, i.e. P, which is used to place a particular element $E_i$ into a specific category, where the classification measure $P_i$ is a function of the numerical parameters $\{S_{ij}\}$. The classification system supplies two important components to the search of the collection. First, ideas about classification and its relationship to objective measures are easily understood by human observers. Second, the classification system can supply detailed information about the local relationship between the numerical parameters used to describe the elements $E_i$ in the collection.

Figure 2:
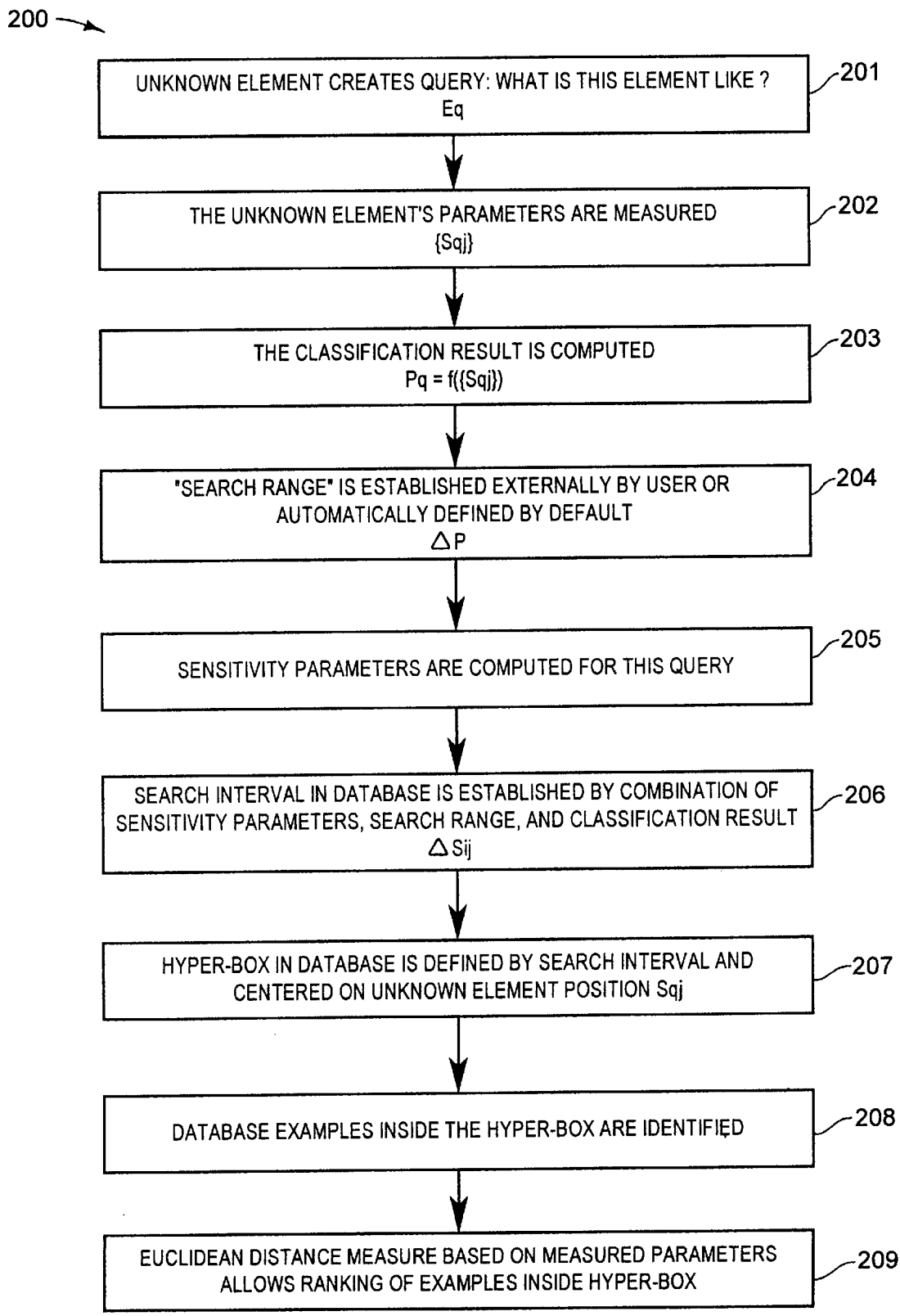
FIG. 2 shows in flowchart form the method steps for querying the database retrieval system according to the invention.

Once the database and classification system is created as described, a query may be made to retrieve elements from the database which are similar or close to a query example, i.e. the unknown element. Reference is made to FIG. 2 which shows in flowchart form a method 200 for database element retrieval. The query example is specified as $E_q$. For example in the context of a cytological specimen testing system, the query example typically comprises a digitized image of a unknown cell (i.e. specimen), and a query is made to the database to retrieve elements which are similar to the unknown cell which forms the query example $E_q$.

Referring to FIG. 2, the first step (block 201) in the method 200 involves creating a query for the unknown element $E_q$, i.e. what is the unknown element $E_q$ similar or close to in the database. The next step (block 202) involves characterizing the query example $E_q$. The query example $E_q$ is characterized by the calculating its numerical parameters $\{S_{qj}\}$. In the context of a cytological specimen testing system, the parameters $S_{qj}$ are derived from features associated with the unknown cell in the same way features or parameters $S_{ij}$ were measured for the elements $E_i$ as described above for FIG. 1. The next step (block 203) involves determining a position for the query example $E_q$ in the classification space. This step comprises computing a classification measure $P_q$ for the query example $E_q$. As described above, the classification measure $P_q$ is determined based on the parameters $\{S_{qj}\}$ for the query example $E_q$ (as determined in step 202 above). The classification measure $P_q$ provides a position for the query example $E_q$ in a portion of the database which as will be described below is characterized as hyper-space or a hyper-box. As will be described below, this hyper-space comprises all the parameters $S_{qj}$ measured for the elements.

The next step (block 204) involves establishing a search range $\Delta P$ for the classification measure P. It will be appreciated that the search range $\Delta P$ is directly related to the degree of dis-similarity which car be tolerated between the query example $E_q$ and the retrieved elements $E_i$. As a result, the search range $\Delta P$ is arbitrary and may be established externally by the user or defined automatically by default. An advantage of utilizing a search range $\Delta P$ defined by the user is that the use of a classification measure carries an intuitive meaning for the human observer that is not present in the individual numerical parameters. In addition, the requirement for the selection of a multitude of search bounds, i.e. $\{\Delta S_{qj}\}$, is replaced by a single search bound, $\Delta P$. Another example allows the human operator to select an acceptable number of elements for the search to be useful. In this case the search bound, $\Delta P$, could be initialized at some value (perhaps based on a histogram of "found" elements in the search region) and then increased until the number of elements in the search region matches number requested by the operator or by the automatic system.

The next step (block 205) comprises calculating sensitivity parameters $\{\Theta_{qj}\}$ for each numerical parameter $S_{qj}$. As mentioned above, the classification system is able to provide information about the local relationship between the numerical parameters $\{S_{qj}\}$ in the collection. The sensitivity parameter $\Theta_{qj}$ provides this information. It will be appreciated that the sensitivity parameter $\Theta_{qj}$ comprises the local slope or first derivative of the classification function with respect to each parameter $S_{qj}$ or feature. The sensitivity parameter $\Theta_{qj}$ is embodied in the derivative since a large derivative means that the classification function is sensitive to small changes in the parameter. Accordingly, rather than making the search range the same in all parameter directions, the range is weighted according to sensitivity. For a classification system that is in an analytical form, the sensitivity parameter $\Theta_{qj}$ is defined as follows:

$$\Theta_{qj} = \frac{\delta |P|}{\delta S_{qj}} \frac{S_{qj}}{P}$$

Otherwise, the sensitivity parameter $\Theta_{qj}$ may be calculated numerically so long as the classification surface is known to sufficient numerical precision as follows:

$$\Theta_{qj} = \frac{\Delta P *}{\Delta S_{qj}} \frac{S_{qj}}{P}$$

It will be appreciated that $\Delta P^*$ is the numerical equivalent of the "infinitesimal" change, $\delta|P|$. In order to properly measure the local gradient of the classification hyper-surface, $\Delta P^*$ must be very small. In this regard, a strong distinction must be made between this $\Delta P^*$ and the $\Delta P$ which is used to eventually define the region of the search, i.e. the hyper-box, as will be described below.

Referring to FIG. 2, the next step (block 206) comprises establishing a search interval $\{\Delta S_{qj}\}$ for the numerical parameters $\{S_{qj}\}$ in the database. The search interval $\{\Delta S_{qj}\}$ is based on the classification result $P_q$, the search range $\Delta P$, and the sensitivity parameters $\Theta_{qj}$, as follows:

$$\Delta S_{qj} = \frac{S_{qj}}{\Theta_{qj}} \frac{\Delta P}{P}$$

The sensitivity parameters $\Theta_{qj}$ represent local relationships among the numerical parameters $\{S_{qj}\}$. For example, in some regions of the parameter space, the classification function may show that one of the numerical parameters is more important than some others. This importance is reflected in a large value of the sensitivity parameter, and thus a reduced interval, $\Delta S$ for that particular numerical parameter in the search.

Figure 3:
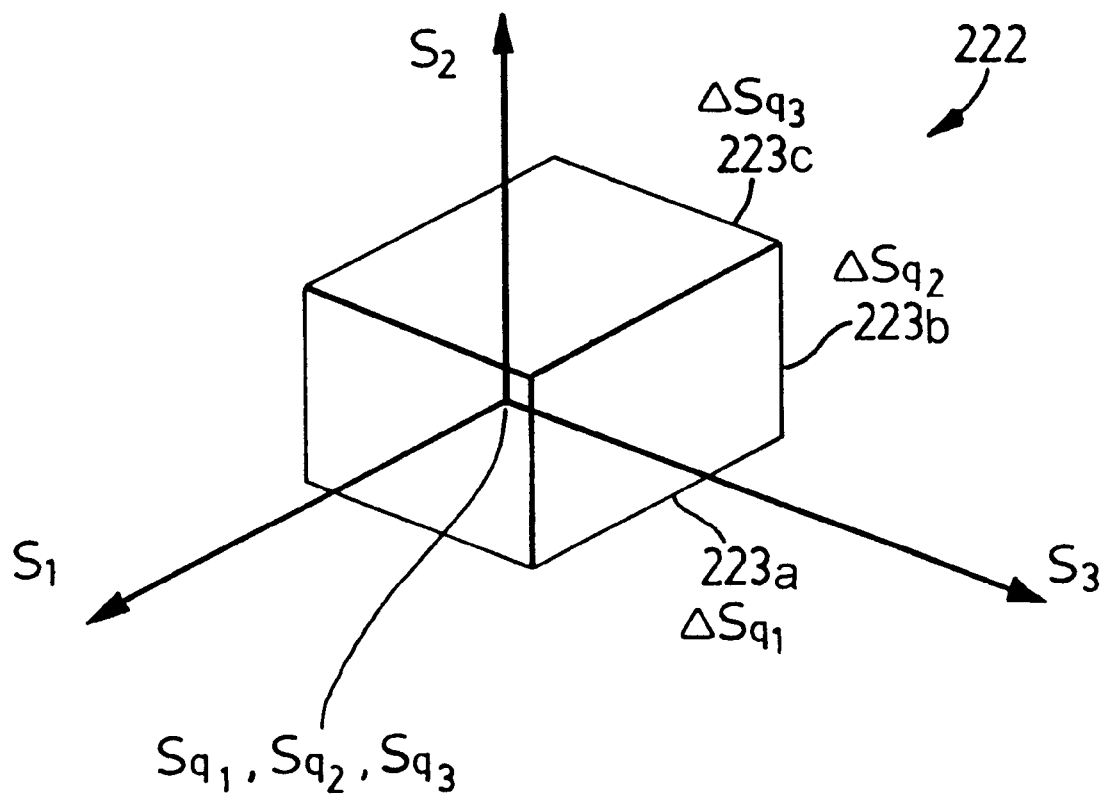
FIG. 3 shows in diagrammatic form a hyper-box for the database retrieval system according to the invention.

Referring back to FIG. 2, the next step (block 207) comprises constructing a hyper-box 222. A hyper-box 222 as shown in FIG. 3 is constructed in the parameter space of the database using the set of numerical parameter intervals $\{\Delta S_{qj}\}$ a "hyper-box" is constructed. As shown in FIG. 3, the hyper-box 222 is centered on the unknown element position $\{S_{qj}\}$ and has sides 223, denoted individually as 223a, 223b and 224b. The length of each side 223 is given by search intervals $\{\Delta S_{qj}\}$ determined above and denoted individually in FIG. 3 as $\Delta S_{q1}$, $\Delta S_{q2}$, and $\Delta S_{q3}$, respectively.

Once the hyper-box 222 has been created, the original database elements $E_i$ which are found in the hyper-box 222 are retrieved as the search results in response to the query. All of the elements $E_i$ in the collection that fall within the hyper-box 222 are considered to be close enough to the query example $E_q$ to be similar to it. For example, in the context of a cytological specimen testing system, the elements $E_i$ found in the hyper-box 222 would comprise groups of cells or cellular clusters that are similar to the unknown cell on which the query example $E_q$ is based. The elements $E_i$ found in the hyper-box are then retrieved for further display or analysis. For example, if the collection of elements $E_i$ has been sorted according to a primary key, secondary key, and tertiary keys (all based on the numerical parameters $\{S_{qj}\}$), then the search procedure can proceed very quickly to determine the occupants of the hyper-box by moving successively from key to key looking only within the boundaries prescribed by $\{S_{qj} \pm \Delta s_{qj}\}$.

An additional step (block 209) in the method 200 comprises ranking the elements $E_i$ of the collection found in the search (i.e. hyper-box 222) according to their "nearness" to the query element $E_q$ using a Euclidean distance measure. Since similarity is represented by distance in the hyper-space of the database, the further calculation of Euclidean distance ;measures provides a means for ranking the search results according to degree of similarity. In the same way that the search region can be defined by the hyper-box 222, any element $E_i$ is ranked according to its distance from the query element $E_q$. To be consistent, the numerical parameter intervals $\{\Delta s_{qj}\}$ are used to normalize the distance measures. Thus, within any search hyper-box 222, each found element $E_1$ can be ranked according to the dimension-less distance as follows:

$$d_i = \left[ \sum_{\Delta S_{qj}} \{S_{qj} - S_{ij}\}^2 \right] 1/2$$

with the ranking formed according to the values of $d_1$. An additional advantage of this ranking is that if the number of elements $E_i$ found in the search is too great, the elements with the largest distance measures, $d_1$, can be eliminated first to bring the total down to the acceptable range.

Figure 4:
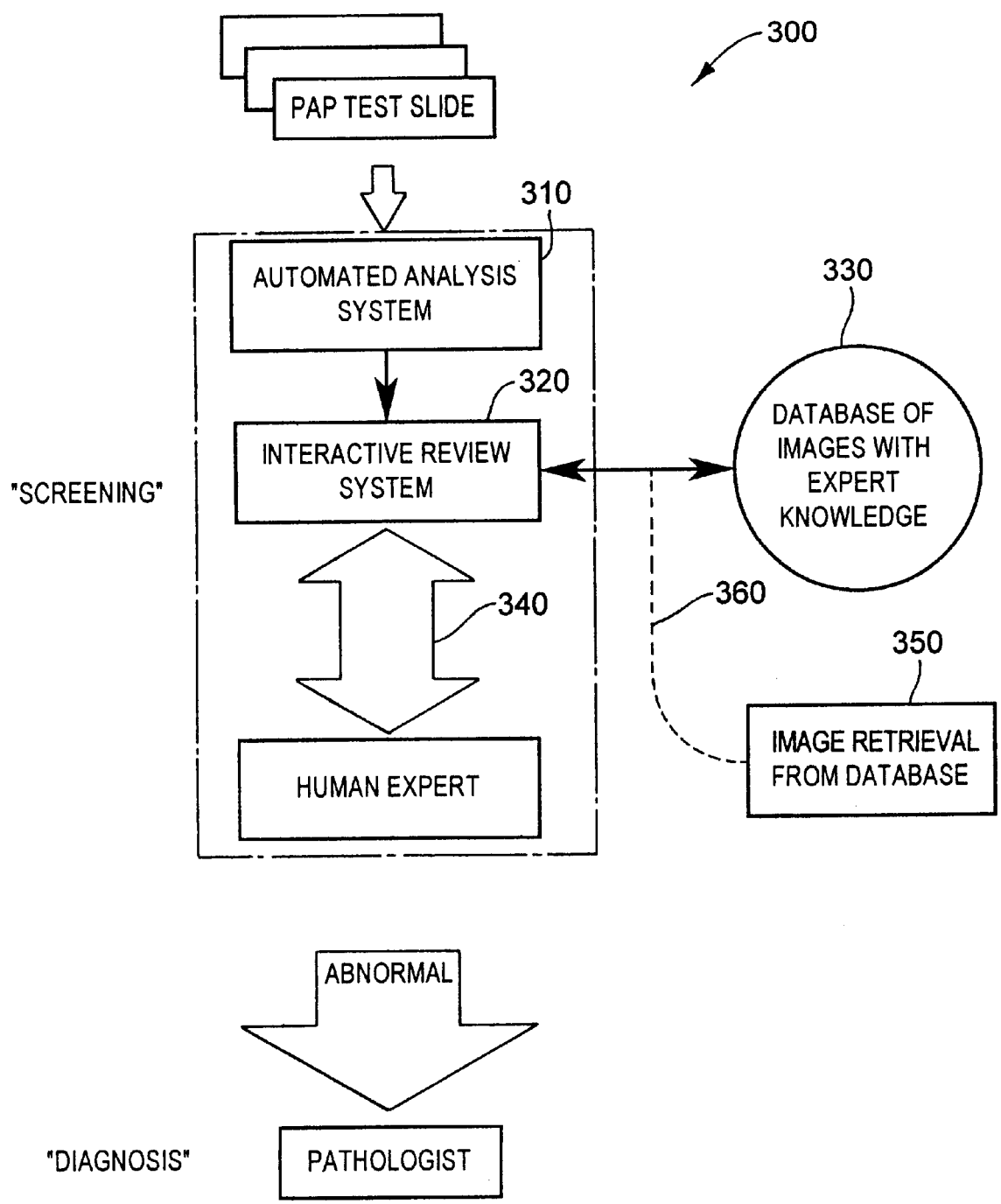
FIG. 4 shows in schematic form an application of the database retrieval system of the present invention to an automated analysis system.

Reference is next made to FIG. 4 which shows the application of the database element retrieval mechanism according to the present invention to an automated cytology system denoted generally by 300.

The Pap test is well-known cytological procedure which comprises a screening for identifying women with pre-invasive lesions of the uterine cervix. The Pap test is performed as a manual, microscopic examination of exfoliated cervical cells in search for a few cells exhibiting neoplastic changes. When applied in the form of a mass screening, the Pap test has been able to achieve dramatic reductions in mortality from cervical cancer.

The overwhelming drawback of the Pap test is reliance on highly skilled, manual labour. Not only does this add tremendous costs, but the throughput remains low and is prone to error. The use of automated systems based on high-speed image analysis and computer processing can, in principle, help to alleviate these problems. However, since the practical evaluation of the Pap test is so complex, it seems clear that a successful machine-based system will continue to benefit from human expert evaluation. A technique for combining the automated system's advantages with those of the human expert comprises interactive or computer-aided review.

As shown in FIG. 4, the automated cytology application 300 comprises an automated analysis module 310, an interactive review module 320, a database 330 for a collection of image elements 350 with expert knowledge.

In this application, the automated analysis module 310 and the interactive review module 320 work to eliminate, through computer analysis, as many of the benign cells as possible. This leaves a residue of "suspicious" cells that require the expertise of a human interpreter denoted by path 340. This residue, which is a small fraction of the total cell population of the specimen, can be represented as an image on a television monitor for the analysis by a human being, or may simply be the position reference of that suspicious cell on the specimen (accessible by automatic or manual microscope stage control). It will be appreciated that by combining the speed of the computer with the experience of the human, great savings can be made in the time taken to render a correct screening decision.

The database element retrieval system described above is utilized during the interactive review of specimens. By using digital representations of the suspicious cells (i.e. suspicious images) as query elements, the system 300 can retrieve (path 360) examples of images 350 that are similar to the suspicious image and the retrieved images are examined by the human expert. Since the retrieved images 350 also contain expert information (as a consequence of being part of the database 330) this information can be used by the human expert to arrive at a screening decision more quickly and with a greater level of confidence.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A database element retrieval system comprising:
   (a) means for storing a plurality of elements, said elements having parameters defining characteristics of said elements, and said elements being stored and classified based on one or more of said parameters;
   (b) means for processing an external query, said means for processing including, (i) means for generating search parameters associated with said query, (ii) means for determining a classification measure for said query, said classification measure being based on the search parameters for said query, and said classification measure providing a measure of similarity between the search parameters for said query and the parameters associated with elements store din the database, (iii) means for setting a search range in the database for said query, (iv) means for establishing a search space in the database, said search space being based on said search range and said classification measure, (v) means for retrieving a plurality of elements from said search space in response to said query.

2. A method for retrieving one or more elements from a database in response to a query, said method comprising the steps of:

(a) generating search parameters associated with said query;

(b) determining a classification measure for said query, said classification measure being based on the search parameters for said query, and said classification measure providing a measure of similarity between the search parameters for said query and the parameters associated with elements stored in the database;

(c) setting a search range in the database for said query;

(d) establishing a search space in the database, said search space being based on said search range and said classification measure;

(e) retrieving a plurality of elements from said search space in response to said query.

3. A method for creating a collection of elements for a database, said elements comprising digital representations of cytological specimens, said method comprising the steps of:

(a) measuring parameters associated with each of the digital representations, said parameters including size, colour, shape or texture of objects appearing in said digital representations;

(b) classifying said elements on the basis of similarities between said measured parameters.

4. A database system for retrieving one or more digital representations of cytological specimens in response to a query, said database system comprising:

(a) means for storing a plurality of digital representations of cytological specimens;

(b) means for determining digital representations in the database which are similar to the query, said similarity being based on measured parameters associated with said digital representations; and (c) means for retrieving said similar digital representations.

5. A method for retrieving one or more digital representations of cytological specimens from a database in response to a query, said method comprising the steps of:

(a) determining one or more digital representations similar to the query, said similarity being based on parameters associated with the digital representations;

(b) retrieving said similar digital representations from the database in response to said query.

6. A database retrieval system for digital representations of cytological specimens, said database retrieval system comprising:

(a) means for storing a plurality said digital representations, said digital representations having parameters defining characteristics of said digital representations, and said digital representations being stored and classified based on one or more or said parameters;

(b) means for processing an external query, said means for processing including, (i) means for generating search parameters associated with said query, (ii) means for determining a classification measure for said query, said classification measure being based on the search parameters for said query, and said classification measure providing a measure of similarity between the search parameters for said query and the parameters with digital representations stored in the database, (iii) means for setting a search range in the database for said query, (iv) means for establishing a search space in the database, said search space being based on said search range and said classification measure, (v) means for retrieving a plurality of digital representations from said search space in response to said query.

* * * * *